United States Patent
Lin et al.

(10) Patent No.: US 6,691,561 B2
(45) Date of Patent: Feb. 17, 2004

(54) RHEOLOGICAL MEASUREMENT PROCESS

(75) Inventors: Ye-Gang Lin, Evansville, IN (US); Vijaykumar Hanagandi, Evansville, IN (US); Ana Isabel Diaz Calderon, Murcia (ES); Rafael Hierro Martin, Murcia (ES)

(73) Assignee: Gerneral Electric Company, Schenectady, NY (US)

( * ) Notice: Subject to any disclaimer, the term of this patent is extended or adjusted under 35 U.S.C. 154(b) by 33 days.

(21) Appl. No.: 10/122,858

(22) Filed: Apr. 15, 2002

(65) Prior Publication Data

US 2003/0192367 A1 Oct. 16, 2003

(51) Int. Cl.[7] .................... G01N 11/00; G01N 11/02
(52) U.S. Cl. .................... 73/54.42; 73/54.01; 73/54.02
(58) Field of Search .................... 73/54.04, 54.07, 73/54.09, 54.11, 54.13, 54.14, 54.42, 54.01, 54.02

(56) References Cited

U.S. PATENT DOCUMENTS

| | | | | |
|---|---|---|---|---|
| 3,841,147 A | * | 10/1974 | Coil et al. ................. | 73/54.11 |
| 3,977,235 A | * | 8/1976 | Topham ..................... | 73/54.04 |
| 4,241,602 A | * | 12/1980 | Han et al. .................. | 73/54.14 |
| 4,680,957 A | * | 7/1987 | Dodd ........................ | 73/54.04 |
| 4,817,416 A | * | 4/1989 | Blanch et al. ............. | 73/54.04 |
| 5,202,395 A | * | 4/1993 | Chambon ................... | 73/54.14 |
| 5,877,409 A | * | 3/1999 | Girling ....................... | 73/54.06 |
| 5,959,195 A | * | 9/1999 | Gottfert ..................... | 73/54.11 |
| 5,974,866 A | | 11/1999 | Tjahjadi et al. ............ | 73/54.11 |

FOREIGN PATENT DOCUMENTS

| | | | | |
|---|---|---|---|---|
| DE | 129239 | * | 1/1978 | ................ 73/54.04 |
| DE | 294091 | * | 9/1991 | ................ 73/54.09 |
| JP | 60-100739 | * | 6/1985 | ................ 73/54.04 |

\* cited by examiner

*Primary Examiner*—Daniel S. Larkin (57) ABSTRACT

A method and apparatus for measuring the rheological properties of a polymer melt includes flowing the polymer melt from a first reactor to a device through a conduit at a predetermined flow rate, measuring a first pressure of the polymer melt at a first location in the conduit, measuring a second pressure at a second location downstream from the first location, measuring a temperature at a third location in the conduit, wherein the third location is between the first location and the second location, and calculating the rheological property of the polymer melt as it flows through the conduit. The method and apparatus do not require diversion of the polymer melt from the main process stream.

21 Claims, 4 Drawing Sheets

RHEOLOGICAL MEASUREMENT PROCESS

BACKGROUND OF THE INVENTION

The present disclosure generally relates to apparatuses and methods for measuring and controlling the viscosities of liquids.

Viscosity measurement of liquids is a procedure used in the characterization of many liquid products including polymers and polymer melts. The testing is typically performed off-line on a small scale in a laboratory setting. Samples of the polymer melt are periodically withdrawn from the main process stream during the manufacturing process and carried to the laboratory to be tested and characterized. The test results are then used to tweak and adjust the manufacturing process to obtain a targeted polymer melt quality. Data obtained in this manner is not representative of the ongoing manufacturing process since a significant time delay in obtaining the data exists.

More recently, efforts have been directed to reducing the response time by measuring polymer melt properties during the manufacturing process itself in order to provide better control over the quality of the polymer melt. Measurement during the manufacturing process, however, requires equipment that is relatively easy to use, maintain, and rugged enough to withstand the operating conditions to which the equipment will be exposed. In order to be effective, the equipment must be responsive, and must avoid disturbing the manufacturing process being monitored.

Among the more successful rheometers employed during the manufacturing process are capillary rheometers that divert a portion of the polymer melt from the main stream of molten plastic, conduct measurements on the diverted polymer melt, and then simply purge the polymer melt out to the atmosphere. These types of rheometers are often referred to as on-line rheometers. Other types of capillary rheometers have been developed in which the diverted melt is returned to the main stream, thereby eliminating waste and the additional steps associated with the purge stream. These types of capillary rheometers are often referred to as in-line rheometers.

Capillary rheometers usually employ a first metering pump, such as a gear pump, to feed a capillary passage with a controlled flow of the diverted polymer melt. In the case of in-line rheometers, a second metering pump is employed to return the diverted melt to the main stream. In capillary viscosity measurement, a pressure drop of a liquid flowing through the capillary is used to measure its viscosity. Typically, the capillary has a very small internal diameter, such as 3 mm or less. When a liquid exhibits a high resistance to flow through the capillary, its viscosity is high, and vice versa.

In using the capillary measurement technique, the equation for determining absolute viscosity at a given temperature, which is known as the Poiseuille equation, is shown in equation (I):

$$\eta = \frac{\pi(\Delta P)r^4}{8LF} \tag{I}$$

where $\eta$ is the viscosity of the liquid in poise or grams per second-centimeter, and $(\Delta P)$ is the pressure drop across the capillary in dynes-second per square centimeter; F is the flow rate through the capillary in cubic centimeters per second; L is the length of the capillary in centimeters, and r is the internal radius of the capillary in centimeters.

The actual process of measuring viscosity offline with capillary rheometers is time consuming. Each measurement of the drop time through the capillary requires from three to fifteen minutes, depending on the viscosity of the polymer melt, and must be duplicated in order to obtain a value that can be relied upon. If the second drop time is not close enough to the first, a third, or even fourth drop time must be obtained. The complete viscosity determination, from sample equilibration to measurement, and then through to viscometer cleaning, typically takes from twenty to forty minutes. As a result, the data obtained from capillary rheometers is not representative of the actual ongoing manufacturing conditions.

Non-capillary viscometers have also been developed to measure the viscosity of multiple liquid samples as well as melt flows. Such viscometers include rotation viscometers. A typical rotation viscometer comprises two concentric cylinders, the inner or outer cylinder being rotated in or rotated around the fixed outer or inner cylinder. With such a viscometer, the test liquid is placed between two cylinders and either of the cylinders is rotated around its axis. However, rotation viscometers have several disadvantages. Several measurements must be made on the same liquid sample at different shear stresses. Calculations of viscosity from these devices are troublesome and lead to noticeable errors as they require graphical differentiation of logarithmic values. Special and unstable flows take place at high rotating rates. Furthermore, the devices, which are difficult to clean, must be cleaned after each measurement. Finally, rotational viscometers do not easily render themselves to automation.

Still other non-capillary viscometers have been developed that measure viscosity using different scientific principles. For instance, differential viscometers, such as those made by the Viscotek Company, are based on a fluid analog of the wheatstone bridge, and allow solvents to flow continuously through a bridge network. The differential pressure across the bridge is zero until the sample solution in a reservoir is injected into one of the capillaries. The differential pressure begins to rise until it reaches a steady state value proportional to the specific viscosity of the solution. The viscosity is then calculated from an extensive series of equations. Such a device is limited in its viscosity range and measures viscosity by comparison.

Finally, other non-capillary type viscometers have been developed that calculate viscosity by first determining the flow rate of a liquid passing from a vessel at a given pressure to a vessel at a lower pressure and by the change rate of the internal vessel pressure. Such devices calculate the viscosity of the liquid from shear stress and shear rate by using a lengthy array of calculations. While each of these viscometers has proven superior to the bulb-type capillary viscometer, they still require extensive time to operate and are often not fully automated. Many of these types of devices are limited in their viscosity measurement range.

Accordingly, there remains a need for a method of determining the real-time viscosity and rheology of a polymer melt.

SUMMARY OF THE INVENTION

Disclosed herein is a method for measuring, in real time, rheological properties of a polymer melt. The method comprises flowing a polymer melt from a first reactor to a device through a main conduit at a predetermined flow rate, wherein substantially all of the polymer melt flowing from the reactor to the device flows through the main conduit; measuring a first pressure of the polymer melt at a first location in the main conduit; measuring a second pressure of the polymer melt at a second location in the main conduit downstream from the first location; measuring a temperature of the polymer melt at a third location intermediate to the first location and the second location; and calculating a rheological property of the polymer melt as it flows between the first and second locations of the main conduit.

An apparatus for measuring a property of a polymer melt comprises means for containing a polymer melt under pressure; means for flowing the polymer melt at a defined flow rate through a conduit from the containing means to a device, wherein substantially all of the polymer melt flowing into the device flows through the conduit; pressure sensing means for measuring a first pressure of the polymer melt at a first location in the conduit and producing a first pressure signal, and for measuring a second pressure at a second location in the conduit and producing a second pressure signal, wherein the second location is downstream from the first location; temperature sensing means disposed between the first and second locations for measuring a temperature of the polymer melt and producing a temperature signal; and processor means responsive to the temperature and pressure signals for determining a rheology property of the polymer melt, wherein the processor means is in operable communication with the pressure sensing means, the temperature sensing means and the means for flowing the polymer melt through the conduit.

The rheological property is selected from the group consisting of mass flow rate ("MFR") and mass volume flow rate ("MVR"). MFR is calculated from a formula comprising:

$$MFR = \rho \left[ \frac{Qc \, \exp^{(-D/T)}}{\left( \frac{[0.5(1-a)(P1+(P2-b))]}{a} \right)^{(1+n)}} \right] + d$$

P1 is a measurement of the pressure at the first conduit location, P2 is a measurement of the pressure at the second location, T is a measurement of the temperature at the third location, a, b, c, d, D, n, ρ, are constants, and Q is the defined flow rate of the polymer melt.

MVR is calculated from a formula comprising:

$$MVR = \frac{Qc \, \exp^{(-D/T)}}{\left( \frac{[0.5(1-a)(P1+(P2-b))]}{a} \right)^{(1+n)}} + d$$

P1 is a measurement of the pressure at the first conduit location, P2 is a measurement of the pressure at the second location, T is a measurement of the temperature at the third location, a, b, c, d, D, n, are constants, and Q is the defined flow rate of the polymer melt.

These and other features will be apparent from the following brief description of the drawings, detailed description, and attached drawings.

BRIEF DESCRIPTION OF THE DRAWINGS

Referring now to the figures, which are exemplary embodiments, and wherein the like elements are numbered alike.

DETAILED DESCRIPTION OF THE INVENTION

Figure 1:
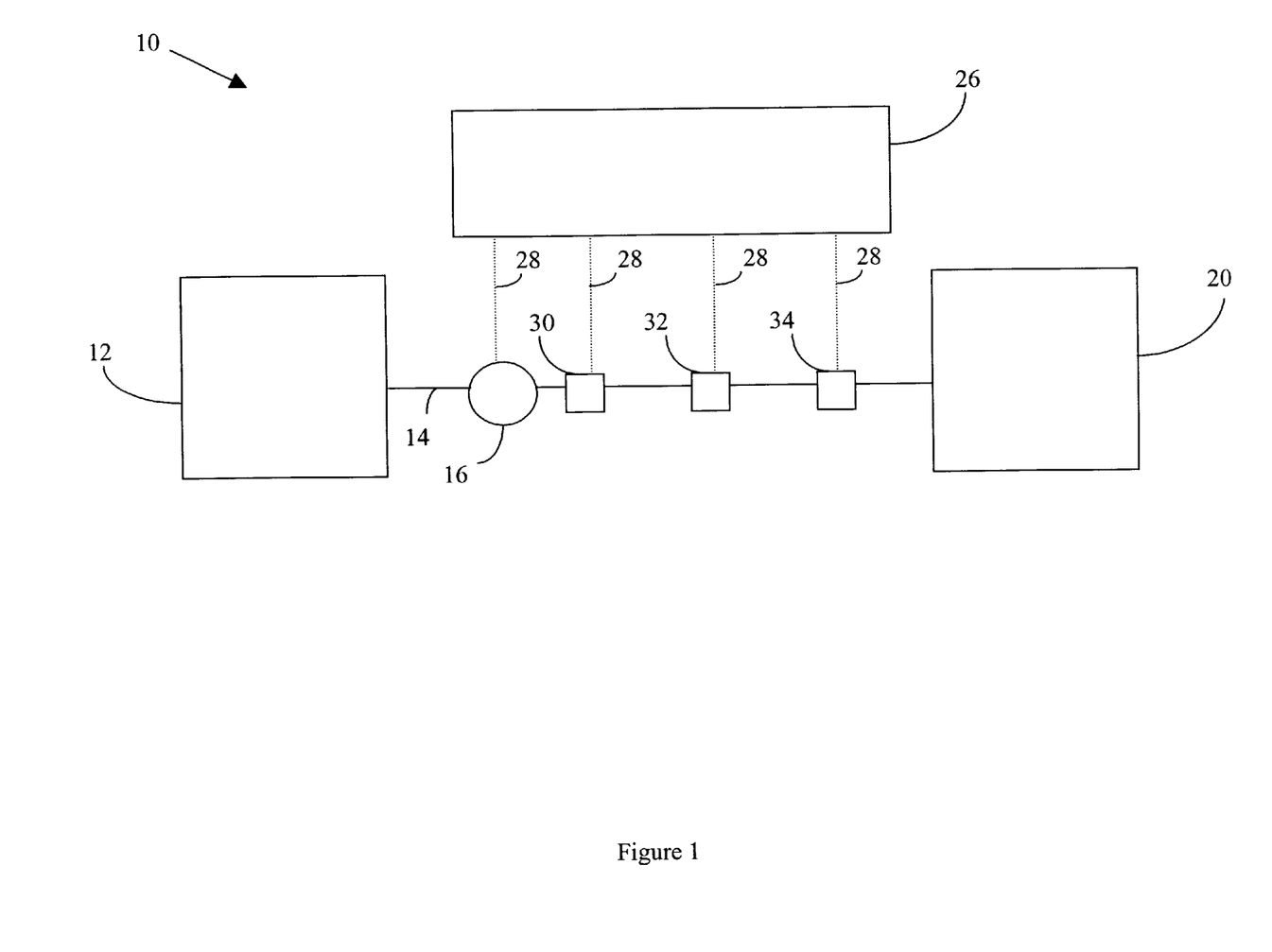
FIG. 1 is a schematic diagram of a continuous reactor for preparing a polymer melt.

Referring now to FIG. 1, a schematic diagram of a continuous polymerization apparatus 10 is depicted. Although the continuous polymerization apparatus 10 is shown, it should be understood that the apparatus is exemplary only, and other suitable apparatus may be used, wherein it is generally desirable to determine the real-time liquid properties of a liquid passing through a conduit.

The illustrated apparatus 10 includes a reactor 12 that contains a polymer melt. More preferably, the polymer melt is a finished polymer that is free from further polymerization and changes in rheological properties. The reactor 12 may comprise one or more interconnected reactors (not shown) for polymerizing monomers to produce a desired polymer. The reactor 12 includes a conduit 14 in fluid communication with a device 20. A metering pump 16, or the like, is connected to conduit 14 to flow the finished polymer melt contained in the reactor 12 at a defined flow rate through conduit 14 to device 20. Device 20 may comprise an extruder, a molding apparatus, another reactor, and the like.

Pressure probes 30, 34 and at least one temperature sensor 32 are disposed in the conduit 14 downstream from the metering pump 16. The temperature sensor 32 is positioned in the conduit 14 preferably at a location intermediate to the location of pressure probes 30, 34 and provides an output signal corresponding to a temperature of the polymer melt as it flows between the pressure probes 30, 34. Optionally, more than one temperature sensor may be disposed between the pressure probes 30, 34 to provide a temperature average of the polymer melt as it flows between pressure probe 30 and pressure probe 34. The pressure probes 30, 34, provide output signals indicative of the pressure, P1, P2, at the probes respective location. Optionally, more than one pressure probe can be employed to provide redundancy in the melt property calculations, which will facilitate pressure sensor failure detection.

The apparatus 10 further includes a processor 26. The processor 26 includes electrical lines 28 in electrical communication with the metering pump 16, for measuring the flow rate of the polymer melt through conduit 14, the pressure probes 30, 34, and the temperature sensor 32. The processor 26 receives output signals generated by the pressure probes 30, 34 and temperature sensor 32 to determine, in real-time, the viscosity of the polymer melt as it flows through conduit 14. The term "real time" refers to a rheological property measurement of the polymer melt as it is flowing through the conduit between pressure probes 30, 34, i.e., a rheological property measurement of the polymer melt that is representative of the actual ongoing manufacturing conditions, thereby advantageously avoiding the delays caused by diverting a portion of the polymer melt from a main conduit into a separate capillary type viscometer or the like.

The processor 26 converts the output signals to a rheological property measurement by execution of certain mathematical functions or algorithms derived from fundamentals of fluid mechanics and rheology. For example, the processor 26 can use the flow rate, pressure and temperature information to determine a Melt-Mass Flow Rate ("MFR", e.g., in grams/10 minutes), or a Melt Volume-Flow Rate ("MVR", e.g., in cubic centimeters/10 minutes) for the polymer melt. The MFR, and/or MVR are standards commonly used in the plastics industry for providing a measure of the polymer melt viscosity.

The viscosity (η) of the polymer melt can be determined according to the following mathematical relationship shown in Equation (II)

$$\eta = \frac{B(P1 - P2)}{Q} \quad \text{(II)}$$

wherein B is a constant determined from the geometry of the conduit 14, P1 is the pressure as measured by pressure probe 30, P2 is the pressure as measured by pressure probe 34, and Q is the volumetric flow rate of the polymer as determined by metering pump 16. The geometry B represents the volume of the conduit as defined by the location of the pressure probes 30, 34. Equation (II) is a variation of the Poiseuille equation described above.

The geometry B of conduit 14 can be readily ascertained using the relationship shown in Equation (II) by flowing a polymer melt at a constant temperature having a known η, ΔP, and Q. In this manner, the geometry B may be determined prior to or during a continuous polymerization and/or an extrusion process. More preferably, the geometry B is determined prior to the continuous polymerization and/or extrusion process. Once the geometry B is determined, its value may be stored in the processor 26 and used to provide real-time viscosity measurements.

The flow rate Q is determined from the speed of the metering pump 16 as determined by the processor 26. Since the speed of the metering pump 16 is known with precision, real-time viscosity measurement can be determined with a high degree of accuracy.

The actual or real pressure drop (ΔP=P1 (actual)−P2 (actual)) as the polymer melt flows through the conduit 14 cannot be accurately obtained from the measured pressure difference since the zero point of commercially available pressure probes (e.g. 30, 34) is known to shift with temperature. Calibration for the actual pressure at zero point would normally require line shutdown whenever the processing temperature of the line changes. However, Applicants have found that accounting for the error attributable to the pressure probe shift can be corrected in accordance with the following mathematical relationship (III).

$$\Delta P_{(corrected)} = 0.5(1-a)(P1+(P2-b)/a) \quad \text{(III)}$$

Figure 2:
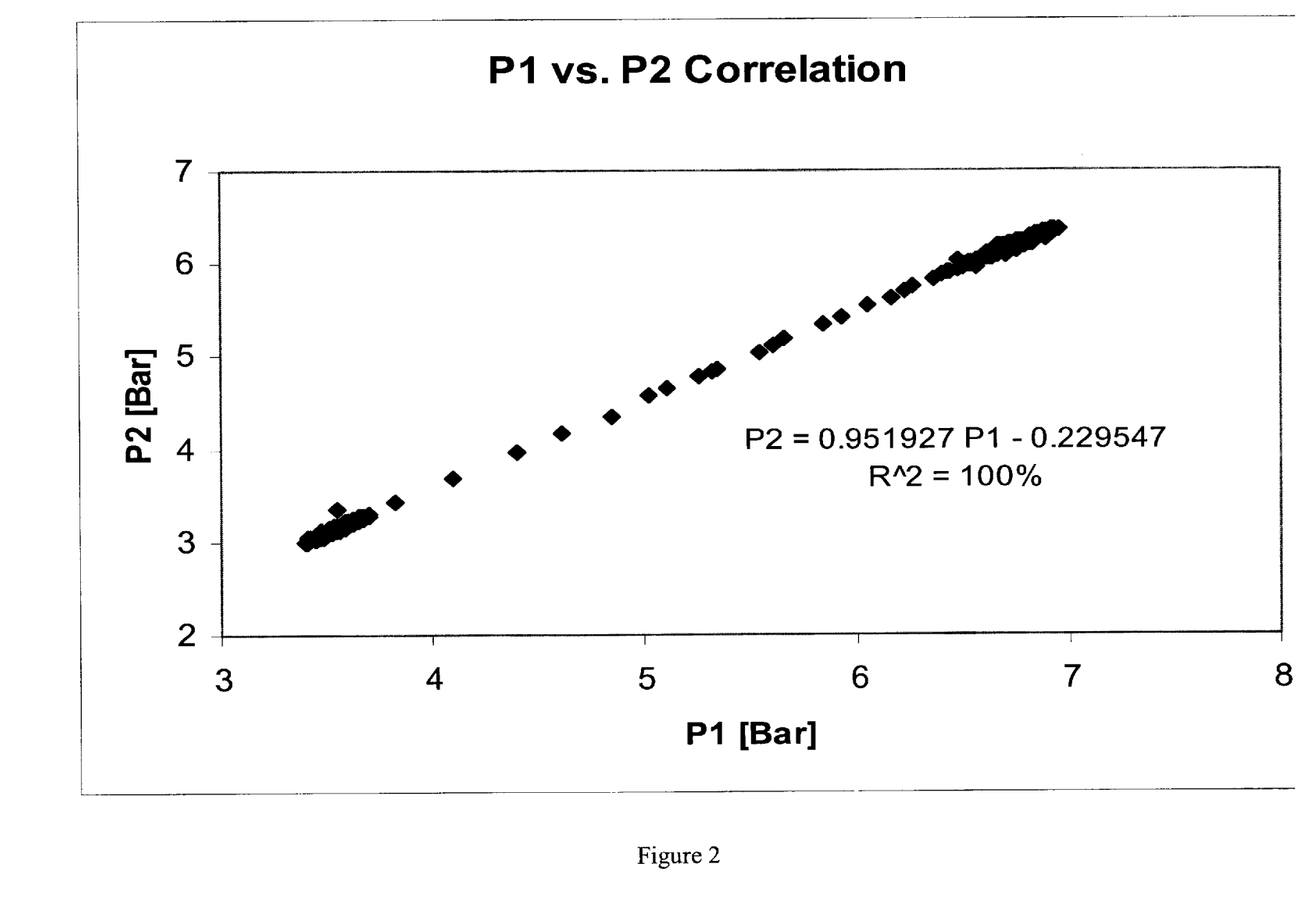
FIG. 2 graphically illustrates a correlation between a pressure of a polymer melt measured at a first location in a conduit and a pressure of the polymer melt measured at a second location in the conduit.

The terms a and b are constants determined by correlating P1 with P2, and wherein $P1_{(actual)} = P1_{(measured)} + \text{error 1}$, and $P2_{(actual)} = P2_{(measured)} + \text{error 2}$. A correlation of P1 versus P2 is shown in FIG. 2. In this manner, the actual pressure drop (ΔP$_{corrected}$) as the fluid flows through conduit 14 can be closely approximated The processor 26 also utilizes a melt temperature correction factor since the viscosity of the polymer melt is directly dependent upon the temperature. The correction factor, as shown in Equation (IV), accounts for temperature fluctuations within the polymer melt as it flows through the conduit 14.

$$X(T) = C \exp^{(D/T)} \quad \text{(IV)}$$

The terms C and D are constants, and T is the absolute temperature of the polymer melt as measured by the temperature sensor 32.

It is also noted that some fluids exhibit non-Newtonian behavior under stress, also referred to as shear stress. Contributions corresponding to shear stress can be defined mathematically as shown in Equation (V).

$$X(P) = E \Delta P^n \quad \text{(V)}$$

The terms E and n are constants.

As previously discussed, in the plastics industry, the determination of rheological properties, such as MVR and/or MFR, are commonly utilized for characterizing the viscosity of polymer melts, wherein both MVR and MFR are inversely proportional to viscosity. By combining Equations (II) through (V), the relationship between laboratory viscosity measurements and the real time measurement process can be expressed as shown in Equations (VI) and (VII):

$$MVR = \frac{Qc \exp^{(-D/T)}}{\left(\frac{[0.5(1-a)(P1+(P2-b))]}{a}\right)^{(1+n)}} + d \quad \text{(VI)}$$

$$MFR = \rho \left[\frac{Qc \exp^{(-D/T)}}{\left(\frac{[0.5(1-a)(P1+(P2-b))]}{a}\right)^{(1+n)}}\right] + d \quad \text{(VII)}$$

wherein a and b are constants determined from the correlation of P1 and P2. Constants c and d are obtained by line calibration, comparing real time data with laboratory data. The melt density ρ, temperature sensitivity parameter D, and the shear sensitivity parameter n, are characteristics of the polymer melt that can be measured off line using common analytical techniques prior to real time analysis.

Although the mathematical relationships described in Equations (VI) and (VII) can be used to accurately measure MFR and MVR in batch processes, it has been found that for continuous processing lines the correlation between P1 and P2 drifts over time. While not wanting to be bound by theory, it is believed that the correlation drift observed in correlation lines is caused by variations in the process conditions downstream from the pressure probes 30, 34 and/or by variations caused by errors in the pressure measurement. For example, as previously discussed, commercially available pressure probes are known to drift over time leading to measurement error. The correlation drift can be accounted for by recalibrating the constants (a, b, c, d in equations V and VI) and storing these constants in the processor 26. Alternatively, an inline correlation correction factor (CCF) may be used to account for the correlation drift. CCF is defined as the moving average of the correlation drift between P1 and P2 over a predetermined period of time and can be described mathematically as shown in Equation (VII).

$$CCF = e + f\left[\frac{P2-b}{P1}\right] + g\left[P1 - \left(\frac{(P2-b)p2}{P1}\right)\right] \quad \text{(VII)}$$

The terms e, f, and g are constants. The correlation correction factor can then be applied to Equations (V) and (VI) to account for the shift in correlation between the pressure probes as shown in Equations (VIII) and (IX).

$$MVR = \frac{Qc \exp^{(-D/T)}}{\left(\frac{[0.5(1-a)(P1+(P2-b))]}{a}\right)^{(1+n)}} + d - CCF \quad \text{(VIII)}$$

-continued $$MFR = \rho \left[ \frac{Qc \exp^{(-D/T)}}{\left( \frac{[0.5(1-a)(P1+(P2-b))]}{a} \right)^{(1+n)}} \right] + d - CCF \quad (IX)$$

Advantageously, the use of the correlation correction factor provides a robust process for accurate rheological property measurement in continuous line polymerization manufacturing processes.

EXAMPLE 1

Figure 3:
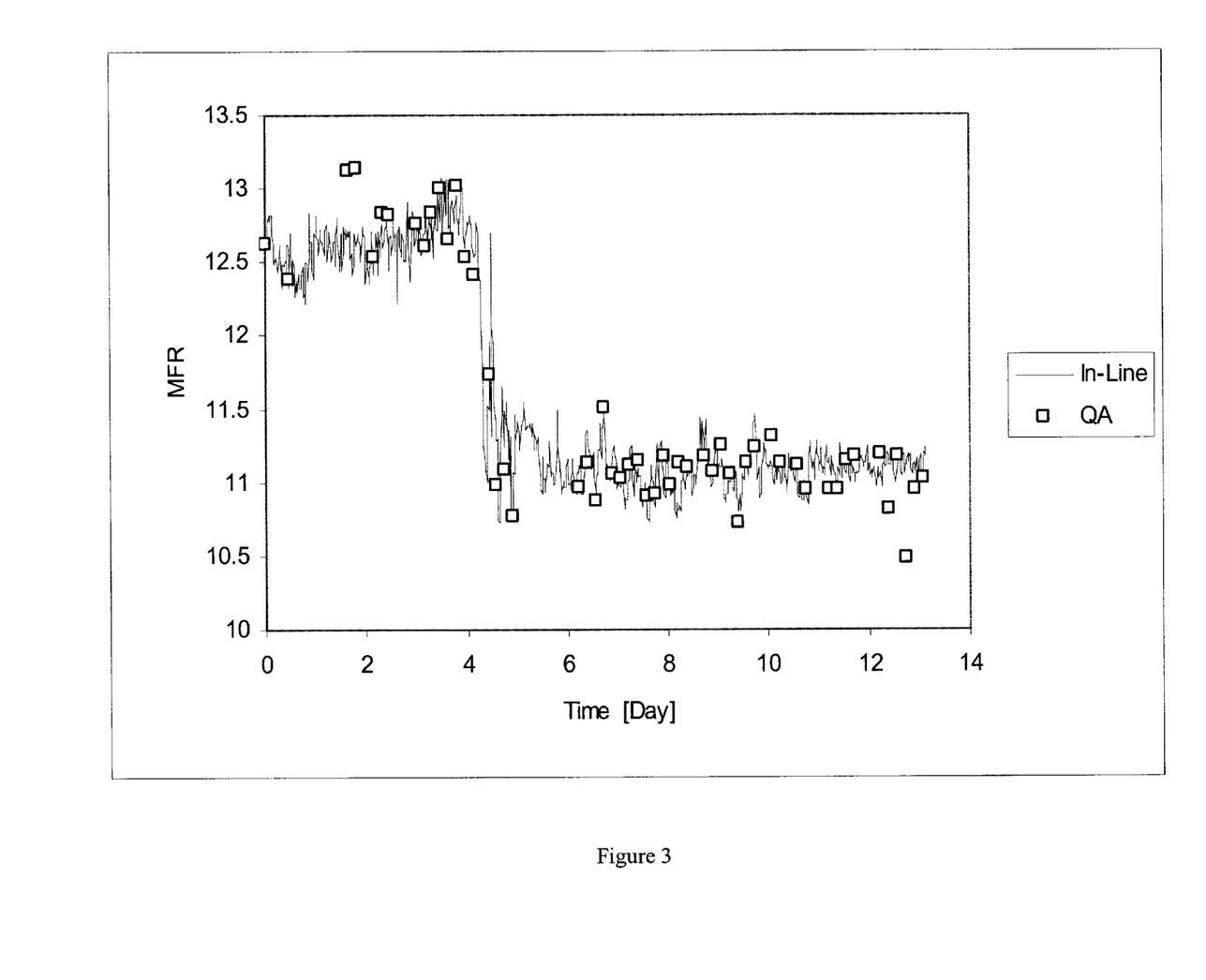
FIG. 3 graphically illustrates a comparison of MFR viscosity measurements obtained by a real time measurement process and an off-line prior art MFR viscosity measurement process.

In this example, real time MFR viscosity measurements from a continuous polymerization process using the apparatus as shown in FIG. 1 was compared to MFR viscosity measurements obtained off-line by periodic sampling of the polymer melt and subsequent analysis in a laboratory. Data was obtained over a 13-day period. The constants utilized for the real time measurement process are as follows: a=0.95193, b=−0.229547, c=2.343E-09, d=0.019, ρ=1.06, D=−10,000, and n=0. The results are shown in FIG. 3.

The results clearly demonstrate the accuracy of the real-time measurement process relative to laboratory sampling and analysis. It is noted that the sampling rate for the real-time measurement process was every 5 seconds. More or less frequent sampling is possible. In contrast, cycle time for the off-line laboratory analysis was at least 4 hours due to the inherent delays associated with sampling, laboratory analysis, and the need for operator intervention.

EXAMPLE 2

In this example, real time MFR viscosity measurements from a continuous polymerization process were compared to MFR viscosity measurements obtained off-line by periodic sampling of the polymer melt and subsequent analysis in a laboratory. The constants utilized for the real time measurement process are as follows: a=0.95193; b=−0.229547; c=2.343E-09; d=0.019; ρ=1.06; D=−10,000; and n=0. Conditional constants included the following: if P1≧4.5 Bar then e=182.973, f=−176.953 and g=−17.022; if P1<4.5 Bar then e=79.963, f=−76.745 and g=−12.704. The results are shown in Table I.

TABLE I

| Time Period (days) | REAL-TIME MFR MEASUREMENT | | COMPARATIVE MFR MEASUREMENT (LAB) | |
|---|---|---|---|---|
| | Mean | Standard Deviation | Mean | Standard Deviation |
| 4 | 12.77 | 0.147 | 12.75 | 0.243 |
| 10 | 11.06 | 0.161 | 11.04 | 0.186 |
| 8 | 12.59 | 0.482 | 12.63 | 0.509 |
| 3 | 11.02 | 0.236 | 11.09 | 0.314 |
| 2 | 10.99 | 0.185 | 11.04 | 0.210 |
| 8 | 12.60 | 0.259 | 12.83 | 0.211 |
| 9 | 11.12 | 0.206 | 11.05 | 0.276 |
| 10 | 12.70 | 0.271 | 12.76 | 0.331 |
| 17 | 11.16 | 0.134 | 11.06 | 0.241 |
| 4 | 12.57 | 0.199 | 12.69 | 0.325 |
| 15 | 10.95 | 0.224 | 11.02 | 0.246 |
| 4 | 12.85 | 0.283 | 12.90 | 0.324 |

The long-term data comparison shows that the real-time measurement process is robust and provides accurate viscosity information consistent with the results obtained from laboratory analysis. It is noted that on average, each periodic laboratory measurement required in excess of about 4 hours per sample, whereas the real time measurement process was substantially instantaneous and is representative of the actual ongoing manufacturing conditions.

The data also suggests that the standard deviation for the real-time measurement process was smaller than the laboratory results. Considering that the process standard deviation includes product variation and gage variation in accordance with the following relationship shown in equation (X), it is estimated that the gage error is significantly lower with the real-time measurement process than the laboratory measurement. In other words, based on the data shown in Table I, the real-time measurement data is equal to or more accurate than the laboratory obtained data.

$$\sigma^2(\text{process}) = \sigma^2(\text{product}) + \sigma^2(\text{gage}) \quad (X)$$

Advantageously, the present disclosure provides methodology for real time rheological property measurement that is representative of the actual ongoing manufacturing conditions. The delays noted in the prior art are avoided, e.g., a reduction in time of several hours for off-line measurement to fractions of seconds for the present in-line measurement process. Moreover, since the main conduit for the polymer melt is utilized in the process, cleaning is not necessary after each measurement. The process can be employed for continuous line polymerization processes or batch processes. The apparatus for measuring the rheological properties can be easily installed and used anywhere in the manufacturing process flow. Moreover, the process overcomes the previously noted problems associated with pressure probe drifting and as such, does not require zero point adjustment for the pressure probe with changing temperatures.

Figure 4:
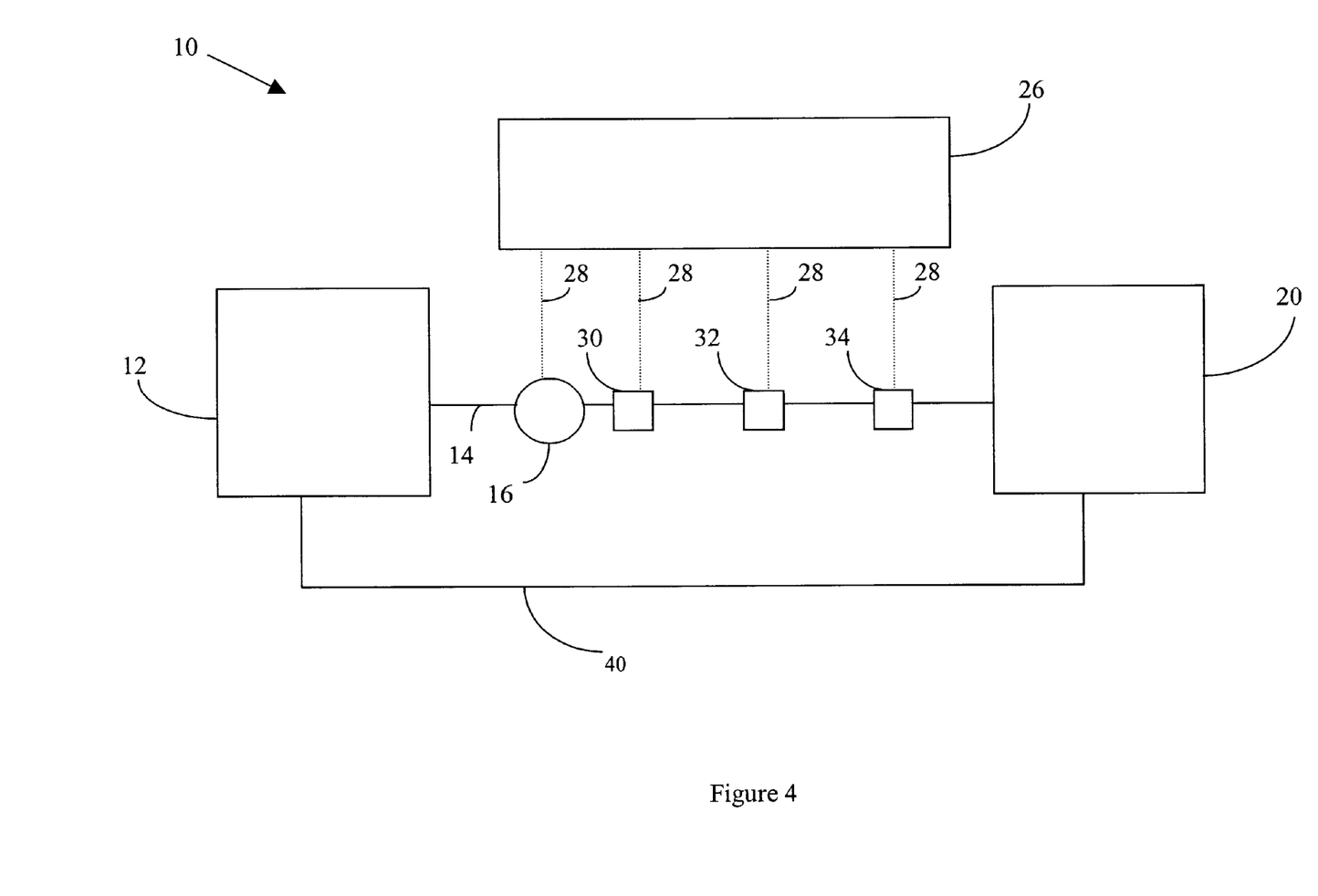
FIG. 4 is a schematic diagram of a continuous reactor including a feedback control loop for preparing a polymer melt.

The results obtained from the real-time rheological property measurement process can also be used to adjust the manufacturing process to obtain consistent polymer quality. For example, as shown in FIG. 4, a feedback control loop 40 can be utilized to adjust one or more of the process parameters. Preferably, the feedback control loop 40 includes an algorithm for adjusting one or more of the operating parameters in the reactor 12 to maintain the polymer consistency in real time. For example, in the event that real time MVR value of the polymer melt is undesirably high or low, the feedback control loop 40 can be used to trigger an increase (or decrease) in pressure of the polymer melt in the reactor 12 to bring the MVR values within specifications. In this example, adjusting a torque control of a reactor agitator in which the polymer melt is contained may be used to vary the pressure indirectly to take advantage of the quick torque to MVR response time. The algorithm for implementing the feedback control loop 40 is well within the skill of those in the art. Alternatively, the consistency of the polymer melt may be controlled using the in-line MVR or MFR process measurements to statistically control, monitor, and adjust the process.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for measuring properties of a polymer melt, the method comprising:
   flowing a polymer melt from a first reactor to a device through a main conduit at a predetermined flow rate, wherein substantially all of the polymer melt flowing into the device flows through the main conduit;
   measuring a first pressure of the polymer melt at a first location in the main conduit;
   measuring a second pressure of the polymer melt at a second location in the main conduit downstream from the first location;
   measuring a temperature of the polymer melt at a third location intermediate to the first location and the second location; and
   calculating one or more of the rheological properties of the polymer melt as it flows between the first and second locations of the main conduit.

2. The method according to claim 1, further comprising measuring a geometry constant of a portion of the main conduit, wherein the portion comprises an area between the first location and the second location.

3. The method according to claim 2, wherein measuring the geometry constant further comprises:
   flowing the polymer melt at a defined flow rate and temperature through the first and second locations of the main conduit, wherein the polymer melt comprises a predetermined viscosity at the defined flow rate and temperature;
   measuring the pressure at the first location;
   measuring the pressure at the second location; and
   calculating the geometry constant according to a formula comprising;

$$\eta = \frac{B(P1 - P2)}{Q},$$

wherein η is the viscosity of the polymer melt, B is the geometry constant, P1 is the pressure at the first location, P2 is the pressure at the second location, and Q is the defined flow rate of the polymer.

4. The method according to claim 1, wherein the first reactor is a fishing reactor, and wherein the polymer melt is free from further polymerization and viscosity changes.

5. The method according to claim 1, wherein the device is selected from the group consisting of an extruder, a molding apparatus, and a second reactor.

6. The method according to claim 1, wherein the one or more rheological properties is selected from the group consisting of mass flow rate, mass volume flow rate, and combinations comprising at least one of the foregoing rheological properties.

7. The method according to claim 1, wherein calculating the one or more rheological properties further comprises calculating an mass flow rate in accordance with a formula comprising:

$$\text{massflowrate} = \rho \left[ \frac{Qc \exp^{(-D/T)}}{\left( \frac{[0.5(1-a)(P1 + (P2-b))]}{a} \right)^{(1+n)}} \right] + d$$

wherein P1 is the first pressure, P2 is the second pressure, T is the temperature, a, b, c, d, D, n, ρ, are constants, and Q is the predetermined flow rate.

8. The method according to claim 7, further comprising correcting a correlation drift between P1 and P2 by applying a correlation correction factor.

9. The method according to claim 8, wherein applying the correlation correction factor further comprises determining a moving average of the correlation drift between P1 and P2 over a period of time and subtracting the correlation drift from the mass flow rate.

10. The method according to claim 1, wherein calculating the one or more rheological properties comprises calculating an mass volume flow rate in accordance with a formula comprising:

$$\text{massflowrate} = \rho \left[ \frac{Qc \exp^{(-D/T)}}{\left( \frac{[0.5(1-a)(P1 + (P2-b))]}{a} \right)^{(1+n)}} \right] + d$$

wherein P1 is the first pressure, P2 is the second pressure, T is the temperature, a, b, c, d, D, n, are constants, and Q is the predetermined flow rate.

11. The method according to claim 10, further comprising correcting a correlation drift between P1 and P2 by applying a correlation correction factor.

12. The method according to claim 11, wherein applying the correlation correction factor comprises determining a moving average of the correlation drift between P1 and P2 over a period of time and subtracting the correlation drift from the mass volume flow rate.

13. An apparatus for measuring a property of a polymer melt, the apparatus comprising:
   means for containing a polymer melt under pressure;
   means for flowing the polymer melt at a defined flow rate through a conduit from the containing means to a device, wherein substantially all of the polymer melt flowing into the device flows through the conduit;
   pressure sensing means for measuring a first pressure of the polymer melt at a first location in the conduit and producing a first pressure signal, and for measuring a second pressure at a second location in the conduit and producing a second pressure signal, wherein the second location is downstream from the fit location;
   temperature sensing means disposed between the first and second locations for measuring a temperature of the polymer melt and producing a temperature signal; and
   processor means responsive to the temperature and pressure signals for determining a rheological property of the polymer melt, wherein the processor means is in operable communication with the pressure sensing means, the temperature sensing means, and the means for flowing the polymer melt through the conduit.

14. The apparatus according to claim 13, wherein the means for flowing the polymer melt at a defined flow rate through a conduit comprises a metering pump.

15. The apparatus according to claim 13, wherein the device is selected from the group consisting of an extruder, a molding apparatus, a reactor vessel, and combinations comprising at least one of the foregoing devices.

16. The apparatus according to claim 13, wherein the temperature sensing means comprises at least one temperature sensor in contact with the polymer melt as it flows between the first and second locations.

17. The apparatus according to claim 13, farther comprising means for automatically adjusting a processing parameter to maintain the rheological property at about a defined value.

18. The apparatus according to claim 17, wherein the means for automatically adjusting a processing parameter comprises a feedback control loop.

19. A method for controlling a rheological property of a polymer melt within a defined range, the method comprising:
   flowing a polymer melt from a first reactor to a device through a main conduit at a predetermined flow rate, wherein substantially all of the polymer melt flowing into the device flows through the main conduit;
   measuring a first pressure of the polymer melt at a first location in the main conduit;
   measuring a second pressure of the polymer melt at a second location in the main conduit downstream from the first location;
   measuring a temperature of the polymer melt at a third location intermediate to the first location and the second location;
   calculating a rheological property of the polymer melt as it flows between the first and second locations of the main conduit; and
   adjusting an operating parameter in the first reactor in response to the calculated rheological property for controlling the calculated rheological property within a defined range.

20. The method according to claim 19, wherein the rheological property is selected from the group consisting of mass flow rate, mass volume flow rate, and combinations comprising at least one of the foregoing rheological properties.

21. The method according to claim 19, further comprising;
   calculating the rheological property of the polymer melt at different locations in the main conduit and comparing the calculated rheological properties for detecting an inaccurate measured pressure.

* * * * *